United States Patent
Kadamus et al.

(10) Patent No.: US 9,981,084 B2
(45) Date of Patent: May 29, 2018

(54) INTEGRATED SPRING-ACTIVATED BALLISTIC INSERTION FOR DRUG DELIVERY

(71) Applicant: Becton, Dickinson and Company, Franklin Lakes, NJ (US)

(72) Inventors: Christopher J. Kadamus, Jamaica Plain, MA (US); Stephen J. Irwin, Arlington, MA (US); Serge Roux, Boston, MA (US); Eric Bené, Lynn, MA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 476 days.

(21) Appl. No.: 14/320,485

(22) Filed: Jun. 30, 2014

(65) Prior Publication Data
US 2014/0316337 A1    Oct. 23, 2014

Related U.S. Application Data

(62) Division of application No. 13/302,956, filed on Nov. 22, 2011, now Pat. No. 8,795,234.

(60) Provisional application No. 61/344,967, filed on Nov. 30, 2010.

(51) Int. Cl.
*A61M 5/158* (2006.01)
*A61M 5/32* (2006.01)

(52) U.S. Cl.
CPC .......... *A61M 5/158* (2013.01); *A61M 5/3287* (2013.01); *A61M 2005/1585* (2013.01); *A61M 2005/1587* (2013.01)

(58) Field of Classification Search
CPC ................ A61M 5/158; A61M 5/3287; A61M 2005/1585; A61M 2005/1587
See application file for complete search history.

(56) References Cited

U.S. PATENT DOCUMENTS

| | | | |
|---|---|---|---|
| 3,572,336 A | * | 3/1971 | Hershberg .......... A61M 5/2066 604/136 |
| 3,918,355 A | | 11/1975 | Weber |
| 4,490,141 A | | 12/1984 | Lack et al. |
| 7,648,494 B2 | | 1/2010 | Kornerup et al. |
| 7,713,258 B2 | | 5/2010 | Adams et al. |
| 8,172,803 B2 | | 5/2012 | Morrissey et al. |
| 8,221,359 B2 | | 7/2012 | Kristensen et al. |
| 8,262,618 B2 | | 9/2012 | Scheurer |
| 8,277,415 B2 | | 10/2012 | Mounce et al. |

(Continued)

FOREIGN PATENT DOCUMENTS

| | | |
|---|---|---|
| JP | 2004-524926 A | 8/2004 |
| JP | 2004-537399 A | 12/2004 |

(Continued)

*Primary Examiner* — Theodore Stigell
(74) *Attorney, Agent, or Firm* — Dickinson Wright PLLC

(57) ABSTRACT

An infusion set has an integrated ballistic inserter that can insert a needle at a controlled high rate of speed to a depth to deliver content to the upper 3 mm of skin surface, and a skin securing, adhesive layer to secure the skin surface at the insertion site such that the inserter that can insert a needle without a risk of tenting of the skin surface. A driving spring of the ballistic inserter is captured within the ballistic inserter, and can be released by user operation, to insert a needle at such a controlled rate of speed.

23 Claims, 6 Drawing Sheets

(56) References Cited

U.S. PATENT DOCUMENTS

| | | |
|---|---|---|
| 8,285,328 B2 | 10/2012 | Caffey et al. |
| 8,287,467 B2 | 10/2012 | List et al. |
| 8,287,516 B2 | 10/2012 | Kornerup et al. |
| 8,306,596 B2 | 11/2012 | Schurman et al. |
| 8,310,415 B2 | 11/2012 | McLaughlin et al. |
| 8,313,468 B2 | 11/2012 | Geipel et al. |
| 8,795,234 B2 | 8/2014 | Kadamus et al. |
| 2004/0044306 A1 | 3/2004 | Lynch et al. |
| 2004/0158207 A1 | 8/2004 | Hunn et al. |
| 2005/0101912 A1 | 5/2005 | Faust et al. |
| 2005/0215979 A1 | 9/2005 | Kornerup et al. |
| 2006/0001551 A1 | 1/2006 | Kraft et al. |
| 2006/0173410 A1 | 8/2006 | Moberg et al. |
| 2007/0093754 A1 | 4/2007 | Mogensen et al. |
| 2007/0219496 A1 | 9/2007 | Kamen et al. |
| 2008/0103463 A1 | 5/2008 | Johnson et al. |
| 2008/0319414 A1 | 12/2008 | Yodfat et al. |
| 2009/0012472 A1 | 1/2009 | Ahm et al. |
| 2009/0124979 A1 | 5/2009 | Raymond et al. |
| 2009/0198191 A1 | 8/2009 | Chong et al. |
| 2009/0198215 A1 | 8/2009 | Chong et al. |
| 2009/0240240 A1 | 9/2009 | Hines et al. |
| 2009/0254041 A1 | 10/2009 | Krag et al. |
| 2009/0326457 A1 | 12/2009 | O'Connor |
| 2010/0049129 A1 | 2/2010 | Yokoi et al. |
| 2010/0160902 A1 | 6/2010 | Aeschilimann et al. |
| 2010/0222743 A1 | 9/2010 | Frederickson et al. |
| 2010/0286714 A1 | 11/2010 | Gyrn et al. |
| 2010/0291588 A1 | 11/2010 | McDevitt et al. |
| 2010/0298830 A1 | 11/2010 | Browne et al. |
| 2012/0253282 A1 | 10/2012 | Nagel et al. |
| 2012/0259185 A1 | 10/2012 | Yodfat et al. |
| 2012/0265034 A1 | 10/2012 | Wisniewski et al. |
| 2012/0277554 A1 | 11/2012 | Schurman et al. |
| 2012/0277667 A1 | 11/2012 | Yodat et al. |
| 2012/0277724 A1 | 11/2012 | Larsen et al. |
| 2012/0283540 A1 | 11/2012 | Brüggemann |
| 2012/0291778 A1 | 11/2012 | Nagel et al. |
| 2012/0293328 A1 | 11/2012 | Blomquist |
| 2012/0296269 A1 | 11/2012 | Blomquist |
| 2012/0296310 A1 | 11/2012 | Blomquist |
| 2012/0296311 A1 | 11/2012 | Brauker et al. |

FOREIGN PATENT DOCUMENTS

| | | |
|---|---|---|
| JP | 2006-501878 A | 1/2006 |
| JP | 2007-510499 A | 4/2007 |
| JP | 2007-511325 A | 5/2007 |
| JP | 2007-536946 A | 12/2007 |
| JP | 2008-536599 A | 9/2008 |
| JP | 2010-531196 A | 9/2010 |
| JP | 2010-533525 A | 10/2010 |
| WO | WO 2006/129196 A1 | 12/2006 |
| WO | WO 2009/010399 A1 | 1/2009 |
| WO | WO 2009/039013 A1 | 3/2009 |
| WO | WO 2010/112521 A1 | 10/2010 |

\* cited by examiner

INTEGRATED SPRING-ACTIVATED BALLISTIC INSERTION FOR DRUG DELIVERY

CROSS-REFERENCE TO RELATED APPLICATIONS

This application is a division of a U.S. patent application of Chris Kadamus et al. entitled "Integrated Spring-Activated Ballistic Insertion For Drug Infusion Device", Ser. No. 13/302,956, filed Nov. 22, 2011, now U.S. Pat. No. 8,795,234, which claims the benefit under 35 U.S.C. § 119(e) of a U.S. provisional patent application of Chris Kadamus et al. entitled "Integrated Spring-Activated Ballistic Insertion For Drug Infusion Device", Ser. No. 61/344,967, filed on Nov. 30, 2010, the entire contents of said applications being incorporated herein by reference.

FIELD OF THE INVENTION

The present invention relates generally to infusion sets, including an integrated inserter for an infusion set, which ensures proper positioning of insertion by using an adhesive to hold an infusion set in position, and a ballistic inserter to first insert a needle at a controlled high rate of speed to a desired intradermal depth, and then hold the needle in an inserted position.

BACKGROUND OF THE INVENTION

A large number of people, including those suffering from conditions such as diabetes use some form of infusion therapy, such as daily insulin infusions to maintain close control of their glucose levels. There are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which an infusion needle or cannula extends. The hub or base has an adhesive which retains the base on the skin surface during use, which may be applied to the skin manually or with the aid of a manual or automatic insertion device. Often, a user is further required to carry and provide a separate inserter. Accordingly, this method of treatment can become cumbersome and wasteful when dealing with the large number of required components.

Currently, most insulin infusion sets deliver insulin to the sub-cutaneous layers of skin using either fixed metal needles or flexible plastic cannulas. Such infusion sets typically deliver insulin 4-10 mm below the skin surface. However, the upper 3 mm of skin surface, the intradermal space, facilitates better drug absorption. Unfortunately, due to the relative thinness of the intradermal layer, inserting a needle at such depth and maintaining an infusion site over an extended period of time within this narrow band is difficult.

Further, most insulin infusion sets typically do not provide any features to isolate the inserted needle from shock or other external forces. Since these infusion sets typically deliver insulin 4-10 mm below the skin surface, shock or other external forces to the set have less effect on the deeper inserted needle. However, where an attempt is made to target the upper 3 mm of skin surface, any shock or movement of the set can adversely affect needle insertion and infusion performance.

Still further, as noted above, most insulin sets require separate inserters, which require the user to carry extra components for treatment, or removable inserters, which require removal from the placed infusion set. However, during such removal, unwanted movement of the set can adversely affect needle insertion and infusion performance. An additional problem encountered by users of such devices is skin surface "tenting" during needle insertion, where the skin surface is deflected somewhat prior to or during needle insertion which makes precisely targeting the upper 3 mm of skin surface difficult.

Accordingly, a need exists for an improved infusion sets that can deliver content to the upper 3 mm of skin surface, the intradermal space, to facilitate better drug absorption, while maintaining a degree of comfort to the user.

SUMMARY OF THE INVENTION

An object of the present invention is to provide an infusion set which can deliver insulin or other medicament to the upper 3 mm of skin surface, the intradermal space, to facilitate better drug absorption, while maintaining a degree of comfort to the user.

Another object of the present invention is to provide an infusion set having an integrated ballistic inserter that can insert a needle at a depth to deliver insulin or other medicament to the upper 3 mm of skin surface.

Another object of the present invention is to provide an infusion set having an integrated ballistic inserter that can insert a needle at a controlled high rate of speed to substantially reduce tenting of the skin surface and insert a needle at a depth to deliver insulin or other medicament to the upper 3 mm of skin surface.

Another object of the present invention is to provide an infusion set having an integrated ballistic inserter in which the overall size of the infusion set is reduced.

Another object of the present invention is to provide an infusion set having an integrated ballistic inserter to eliminate a need for carrying additional inserter components of the set separately from the infusion set.

Another object of the present invention is to provide an infusion set having an integrated ballistic inserter that eliminates the need to remove the inserter components from the placed infusion set and avoids unwanted movement of the set that can adversely affect needle insertion and infusion performance.

Another object of the present invention is to provide an infusion set having a skin securing, adhesive layer to secure the skin surface at the insertion site such that the inserter that can insert a needle with a reduced risk of tenting of the skin surface.

Another object of the present invention is to provide an infusion set that can isolate an inserted needle from external forces such that the needle can be maintained at a depth to deliver insulin or other medicament to the upper 3 mm of skin surface during normal use.

These and other objects are substantially achieved by providing an infusion set having an integrated ballistic inserter that can insert a needle at a controlled high rate of speed to a depth to deliver content to the upper 3 mm of skin surface, and a skin-securing adhesive layer to secure the skin surface at the insertion site such that the inserter can insert a needle with a reduced risk of tenting of the skin surface. A driving spring of the ballistic inserter is configured to insert a needle at a controlled high rate of speed, of 3.3 ft/sec. (1.0 m/sec.) up to and including those greater than 10 ft/sec. (3.0 m/sec.). Depending upon cannula sharpness, such a terminal velocity produces more reliable results for intradermal insertions of short (i.e., 1.5 mm) needle or cannula. The ballistic inserter is integrated with the infusion set to eliminate a need to remove the inserter components from the placed infusion set and avoid unwanted movement of the set.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawings, like reference numerals will be understood to refer to like parts, components and structures.

DETAILED DESCRIPTION OF THE EXEMPLARY EMBODIMENTS

Figure 1:
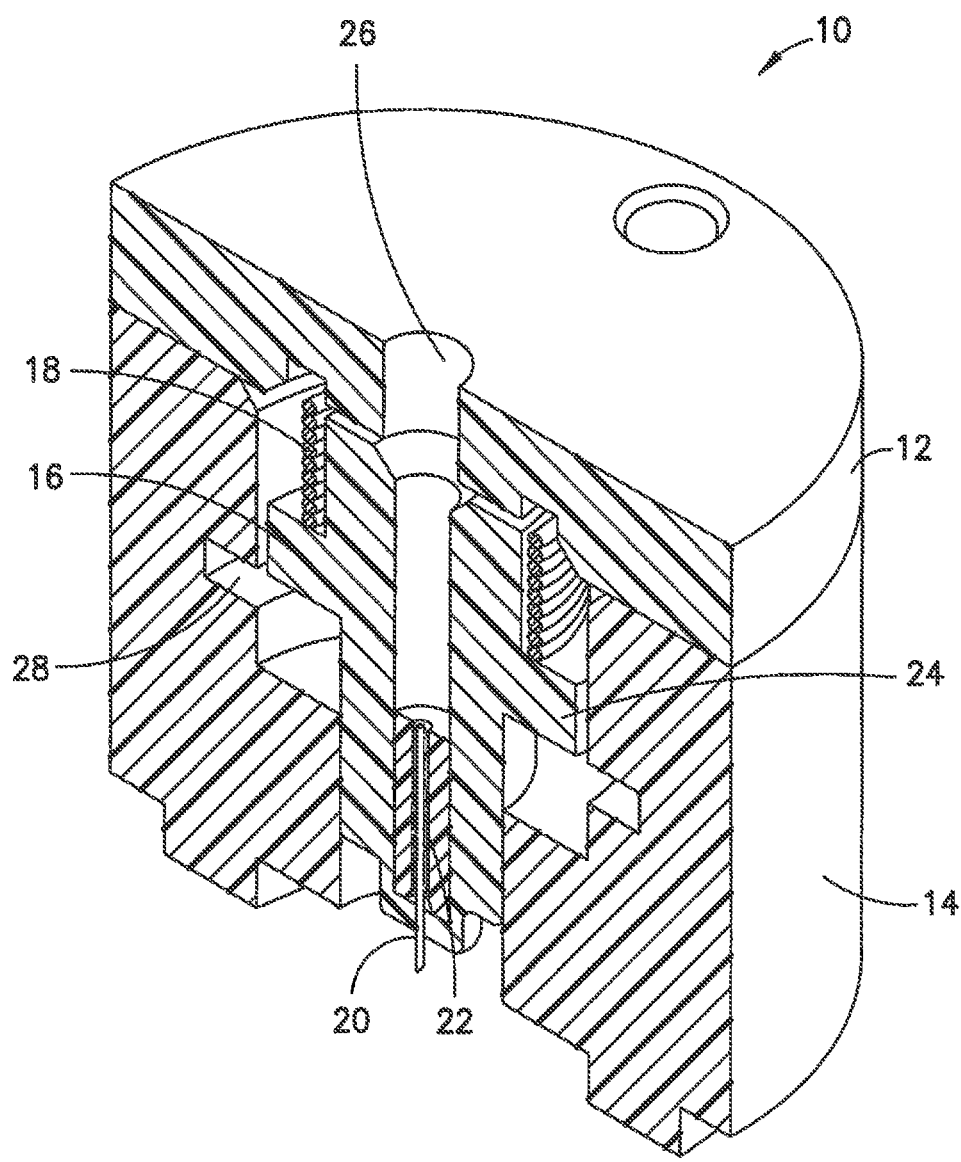
FIG. 1 is a perspective cross-sectional view of an integrated ballistic inserter in accordance with a first embodiment of the present invention.
Figure 2:
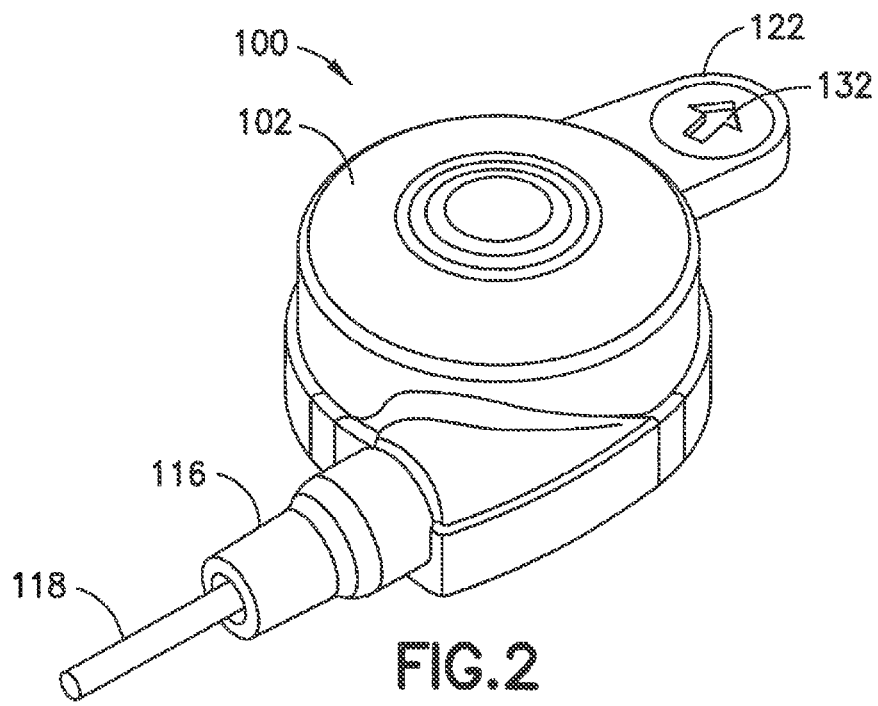
FIG. 2 is a perspective view of an assembled infusion set and integrated ballistic inserter in accordance with a second embodiment of the present invention.
Figure 3:
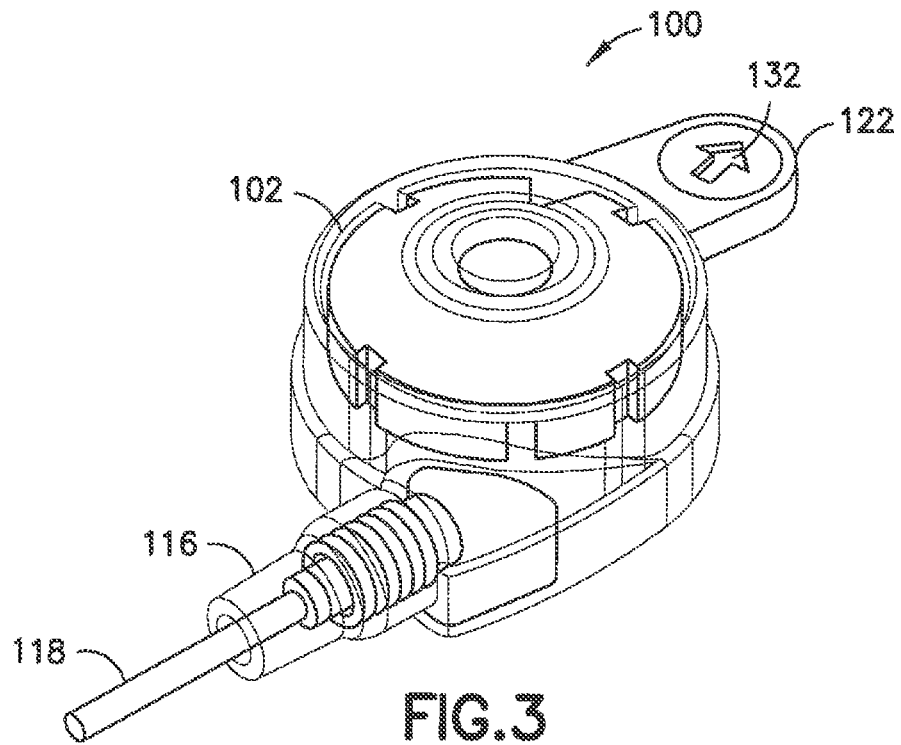
FIG. 3 is a transparent perspective view of the assembled infusion set and integrated ballistic inserter of FIG. 2 in accordance with the second embodiment of the present invention.

The exemplary embodiments of the present invention described below provide a novel means of delivering insulin to the intradermal layers of skin via a standard insulin pump. For example, exemplary embodiments of the present invention provide an infusion set and integrated ballistic inserter to position a needle or cannula to deliver medicament to the upper 3 mm of skin surface, the intradermal space, to facilitate better drug absorption, while maintaining a degree of comfort to the user.

The exemplary embodiments of the present invention deliver insulin to the intradermal layers of the skin via a standard insulin pump or other similar device. By utilizing an integrated ballistic inserter and a skin-securing adhesive, proper insertion and maintenance of the inserted needle in the intradermal space is ensured, while eliminating a need to remove the inserter components from the placed infusion set and avoid unwanted movement of the set.

To do so, the exemplary embodiments comprise an integrated ballistic inserter that can insert a needle of an infusion set at a controlled high rate of speed to substantially reduce tenting of the skin surface and insert the needle at a depth to deliver content to the upper 3 mm of skin surface. A driving spring of the ballistic inserter is configured to insert an exemplary needle at a controlled high rate of speed, of 3.3 ft/sec. (1.0 m/sec.) up to and including those greater than 10 ft/sec. (3.0 m/sec.). Depending upon cannula sharpness, such a terminal velocity produces more reliable results for intradermal insertions of short (i.e., 1.5 mm) needle or cannula. The spring is further used to maintain contact with and prevent refraction of the inserted needle. The inserter components remain with the placed infusion set and do not require removal, yet provide a low-profile set.

The infusion set is also provided with at least one skin-securing adhesive layer to secure the infusion set to the skin surface at the insertion site, such that the ballistic inserter when activated by the user is at the correct position relative to the skin surface, and such that the skin is secured during insertion to further aid needle insertion with a reduced risk of tenting of the skin surface.

In each exemplary embodiment of the present invention described below, standard infusion set elements such as connectors, infusion cannula or needles, adhesives and hubs can be provided. Additionally, the cannula or needle deployment mechanism is provided in the hub itself to eliminate the need of a separate or removable inserter. In each exemplary embodiment, a driving spring is used to provide ballistic insertion of the needle, and then hold the needle in the intradermal or other targeted skin layer using the remaining stored energy in the driving spring. By using such a driving spring, a high-speed insertion is achieved which is considered more reliable for insertion of short (i.e., 1.5 mm) needle or cannula. In the exemplary embodiments, the devices can be provided either preloaded, or can be loaded or armed by the user, who then activates the device via a release button, rotatable tab, pull tab, or other similar mechanism.

Further, after placement and activation, the exemplary embodiments provide means for allowing rotation of the infusion set tubing connector to allow the patient better management of tubing position relative to the pump and provide strain relief from tugging, bumping or other movement that may affect the positioning of the cannula in the skin surface.

In each exemplary embodiment described below, the driving spring can be compressed until it gains a maximum potential energy. This energy is determined by calculating the torsional stresses built up in the spring as it is compressed. By calculating potential energy, and the kinetic energy at the point of needle insertion, an insertion velocity can be calculated. In exemplary embodiments of the present invention, the spring is configured to insert an exemplary needle at a controlled high rate of speed, of 3.3 ft/sec. (1.0 m/sec.) up to and including those greater than 10 ft/sec. (3.0 m/sec.). Depending upon cannula sharpness, such a terminal velocity produces more reliable results for intradermal insertions of short (i.e., 1.5 mm) needle or cannula. The spring diameter, pitch and material all contribute to the spring constant. This constant and the total travel of the spring once released can be manipulated to produce the desired velocity T.

FIG. 1 is a perspective cross-sectional view of an integrated ballistic inserter in accordance with a first embodiment of the present invention. As shown in FIG. 1, the exemplary integrated ballistic inserter 10 comprises a top 12, body 14, and a movable needle hub 16 captured therebetween. In exemplary embodiments of the present invention described below, the housings, hubs and other elements can be constructed of a molded plastic material, polycarbonate, thermoplastic polymer such as polyethylene terephthalate (PET and PETG), or similar materials. As shown in FIG. 1, the needle hub 16 comprises a needle or cannula 20 and hub 22. The needle 20 can preferably comprise a stainless steel or plastic needle/cannula, between 25 gauge and 36 gauge, provided with a single-bevel, tri-bevel or 5-bevel, and be between 1.0 and 10 mm long, but embodiments are not limited thereto. The needle 20 can be bonded to the hub 22 or other needle hub with an adhesive, such as a Loctite/UV cured adhesive, or can be over molded with, or threaded into the septum or hub.

The needle hub 16 further comprises a shoulder 24 which is configured to guide the travel of the needle hub 16 in the body 14 of the inserter 10. Further, a drive spring 18 is captured between the top 12 of the inserter 10, and the shoulder 24 of the needle hub 16 to urge the needle hub 16 toward the skin surface when released. Further, the spring 18 is configured to maintain contact with, and prevent retraction or other movement of the needle hub 16 after insertion. An opening or channel 26 is also provided through the top 12 and needle hub 16 to provide fluid communication to the needle 20 and/or hub 22. A septum (not shown) can be provided in the opening or channel 26 to receive a tube connector.

Figure 4:
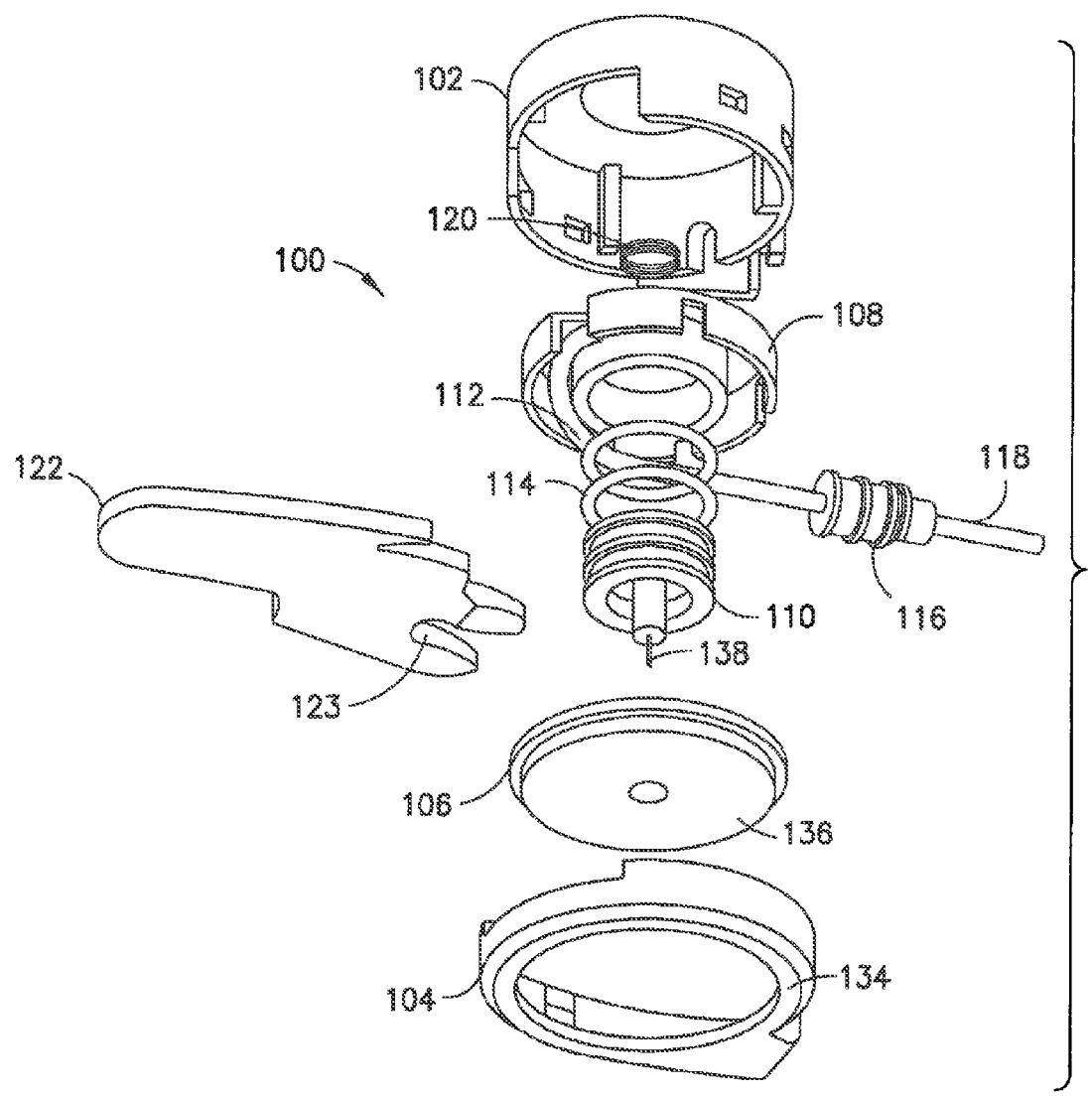
FIG. 4 is an exploded view of the infusion set and integrated ballistic inserter of FIG. 2 in accordance with the second embodiment of the present invention.
Figure 5:
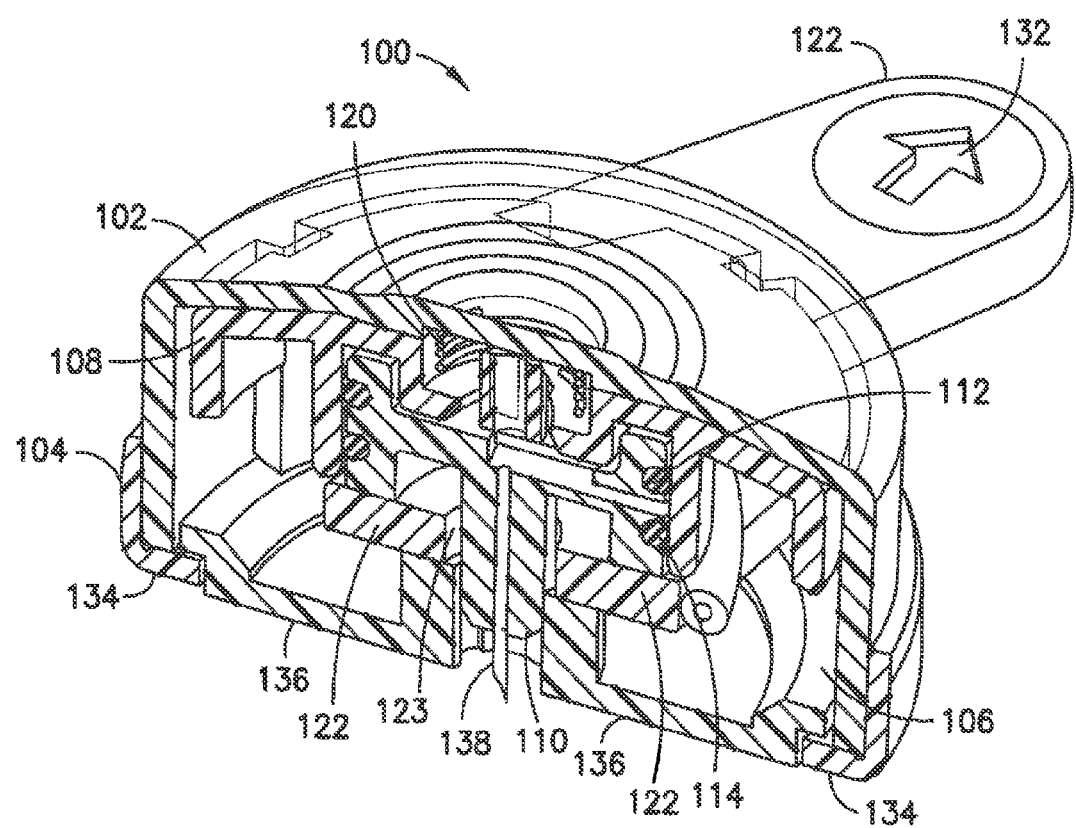
FIG. 5 is a perspective cross-sectional view of the assembled infusion set and integrated ballistic inserter of FIG. 2 in accordance with the second embodiment of the present invention.
Figure 6:
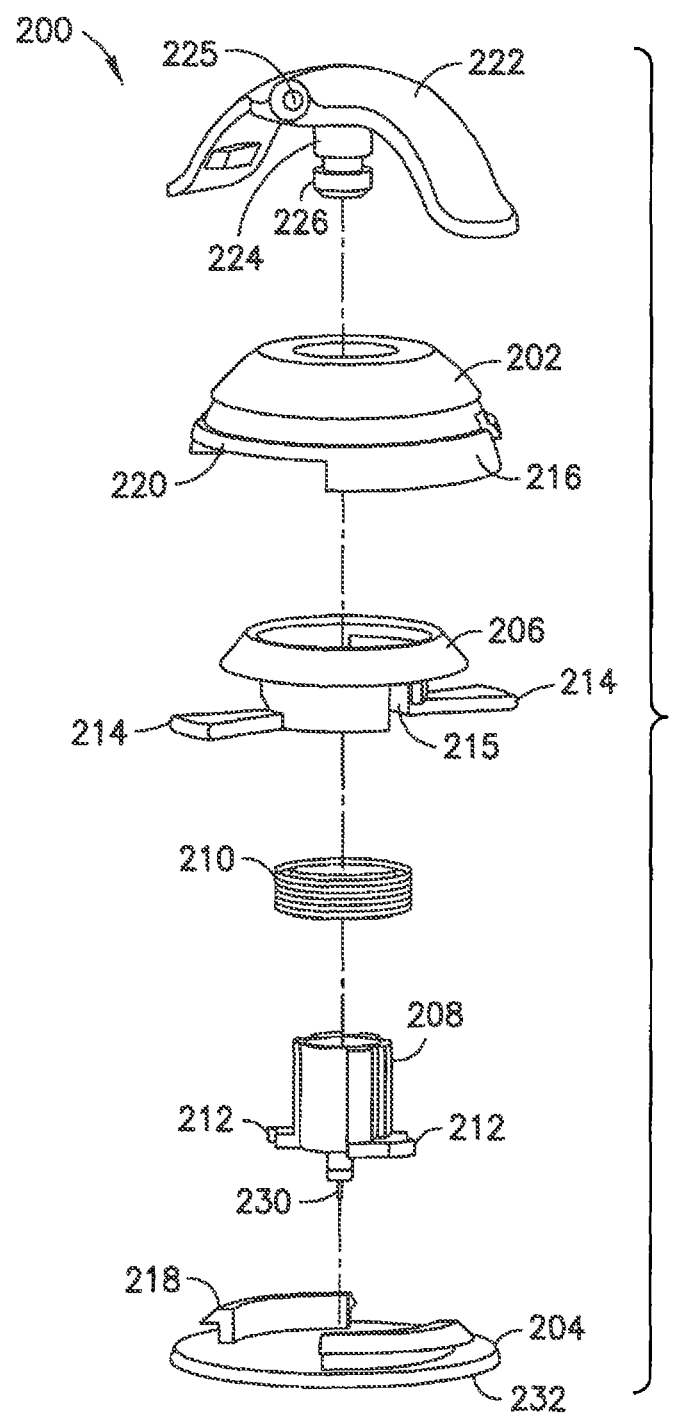
FIG. 6 is an exploded view of an infusion set and integrated ballistic inserter in accordance with a third embodiment of the present invention.
Figure 7:
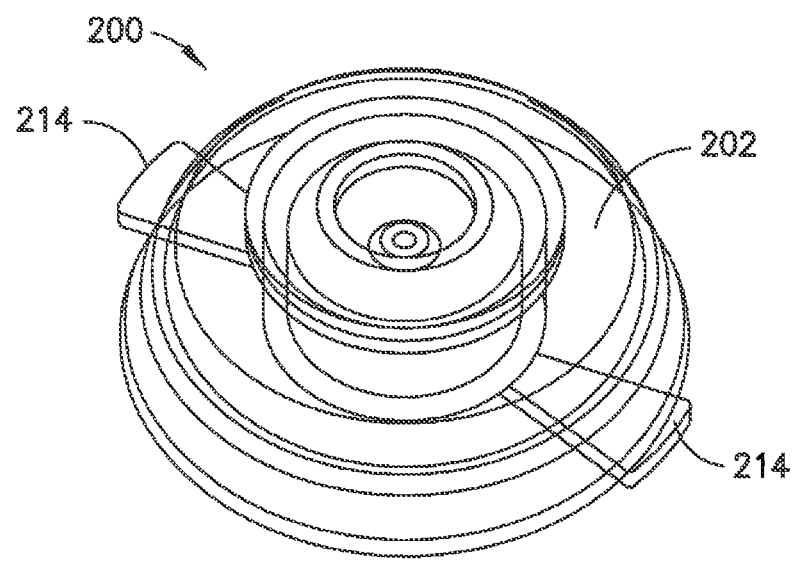
FIG. 7 is a transparent perspective view of the assembled infusion set and integrated ballistic inserter of FIG. 6 in accordance with the third embodiment of the present invention.
Figure 8:
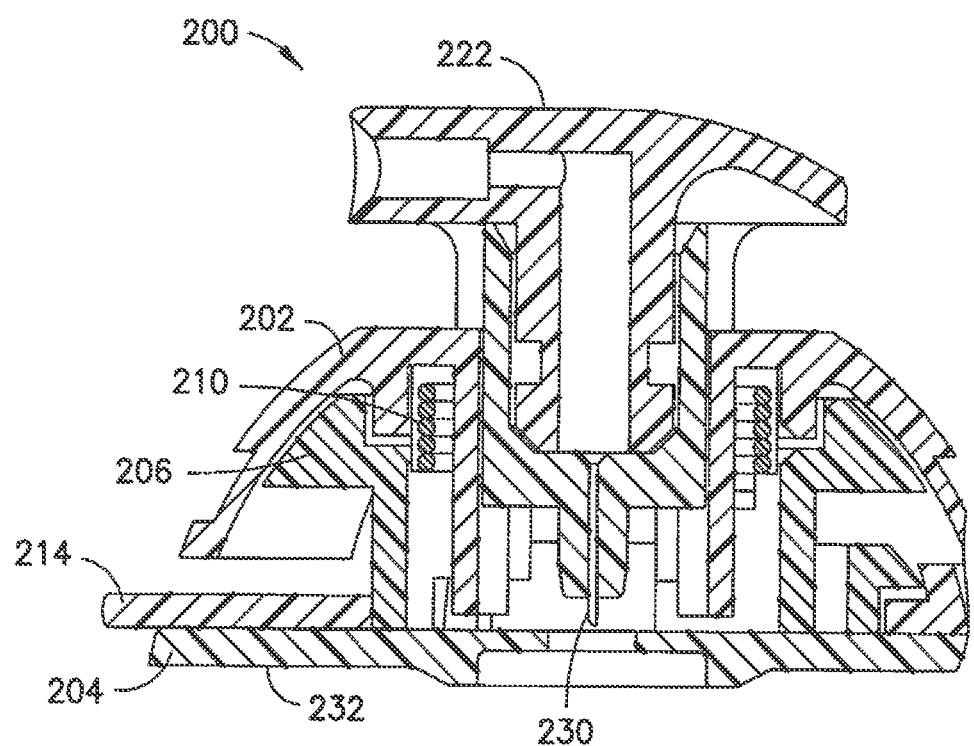
FIG. 8 is a perspective cross-sectional view of the assembled infusion set and integrated ballistic inserter of FIG. 6 in accordance with the third embodiment of the present invention.

The exemplary embodiment of FIG. 1 provides a side entry/connection with a release tab as shown in the embodiments of FIGS. 2-5, or with a turn button as shown in the embodiments of FIGS. 6-8. One or more of a push button or turn button interference or a release tab interference within an opening 28 can be used to hold the needle hub 16 and spring 18 in an up (elevated or retracted) position until released. Further, the top 12, needle hub 16 and spring 18 are able to pivot 360 degrees around the base of the body 14 to provide additional tubing management options for the user.

FIG. 1 and the remaining embodiments described below present an integrated ballistic inserter to illustrate the design and use of a drive spring that can be uniquely designed to achieve a desired insertion velocity and thereafter maintain a force against the needle hub. The inserter components such as the spring remain with the placed infusion set and do not require removal, yet provide a low-profile set. Additional embodiments of the present invention which illustrate release features are described below.

FIGS. 2-5 are views of an integrated ballistic inserter and infusion set 100 in accordance with a second embodiment of the present invention. As shown in the exploded view of FIG. 4, the second exemplary embodiment of the present invention comprises a top 102, base ring 104 and bottom 106. Captured between the top 102 and bottom 106, a body 108, and needle 138 and needle hub 110, are provided. The needle hub 110 is provided with one or more O-rings 112 and 114 that are captured in grooves around an outer circumference of the needle hub 110 to allow the needle hub 110 to rotate freely and provide 360 degree rotation of the tubing attachment. The base ring 104 can be provided with an adhesive layer 134, and the bottom 106 can be provided with an adhesive layer 136, for securing each to a skin surface at the infusion site. The adhesive layers 134 and 136 are separate and can be provided with a single covering. The needle 138 can preferably comprise a stainless steel or plastic needle or cannula, between 25 gauge and 36 gauge, provided with a single-bevel, tri-bevel or 5-bevel, and be between 1.0 and 10 mm long, but embodiments are not limited thereto. The needle 138 can be bonded to the needle hub 110 with an adhesive, such as a Loctite/UV cured adhesive, or can be over molded with, or threaded into the hub.

As shown in FIGS. 4 and 5, the O-rings 112 and 114, and needle hub 110, are slidably captured in a central opening of the body 108. A connector seal 116 and tubing 118 are further provided, which permit the rotation of the needle hub 110 which is connected to the tubing 118. The connector seal 116 can comprise any suitable septum-cannula connection, but embodiments are not limited thereto.

As also shown in FIGS. 4 and 5, a drive spring 120 is captured between the top 102 of the set 100, and the body 108 to urge the body 108 and needle hub 110 toward the skin surface when released. In an exemplary embodiment, the device 100 can further comprise a release tab 122 disposed to extend a U-shaped opening 123 into the body 108 and prevent movement of the needle hub 110 toward the skin surface until pulled from the device by a user accessible tab. An indicator such as arrow 132 can be provided on the tab 122 to identify the tab 122 as a release tab, and to indicate a direction for pulling the tab 122 to activate the device. Once the set 100 is adhered to a skin surface via the adhesive layers 134 and 136 of ring 104 and bottom 106, and the release tab 122 is pulled free from the device, the needle hub 110 is released and the drive spring 120 urges the body 108 and needle hub 110 toward the skin surface and seats the needle 138 of the needle hub 110 into a skin surface (not shown). Further, the drive spring 120 is configured to maintain contact with, and prevent retraction or rearward movement of the needle hub 110 after insertion. The integrated, inserter components such as the spring 120 remain with the placed infusion set and do not require removal, yet provide a low-profile set.

FIGS. 6-8 are views of an integrated ballistic inserter and infusion set 200 in accordance with a third embodiment of the present invention. As shown in the exploded view of FIG. 6, the third exemplary embodiment of the present invention comprises a top 202 and bottom 204. Captured between the top 202 and bottom 204, a body 206 and needle 230 and needle hub 208 are provided. The bottom 204 can be provided with an adhesive layer 232 and covering for securing the bottom to a skin surface at the infusion site. The needle 230 can preferably comprise a stainless steel or plastic needle or cannula, between 25 gauge and 36 gauge, provided with a single-bevel, tri-bevel or 5-bevel, and be between 1.0 and 10 mm long, but embodiments are not limited thereto. The needle 230 can be bonded to the needle hub 208 with an adhesive, such as a Loctite/UV cured adhesive, or can be over molded with, or threaded into the hub.

As also shown in FIGS. 6 and 8, a drive spring 210 is captured between the top 202 of the set 200, and one or more tabs 212 of the needle hub 208, to urge the needle hub 208 toward the skin surface when released. In an exemplary embodiment, the device 200 can further comprise one or more rotary release tabs 214 disposed on the body 206 and extend outward through openings 220 in the top 202 for user access, and prevent movement of the needle hub 208 toward the skin surface until turned by a user.

Prior to activation, the needle hub 208 is held in the up position through contact with the tabs 212 of the hub 208 and the top surface of the body 206. That is, the tabs 212 prevent the hub 208 from entering the body 206 until rotationally moved into alignment by turning the rotary tabs 214 of the body 206. In this position, the spring 210 is compressed between the top 202 of the set 200, and tabs 212 of the needle hub 208. Turning the rotary release tabs 214 on the body 206 serves to align one or more of the tabs 212 or other protrusions of the needle hub 208 with openings 215 in the body 206 which permits the needle hub 208 to pass downward through the body 206. Once the rotary release tabs 214 are turned and the needle hub 208 is released, the drive spring 210 urges the tabs 212 of the needle hub 208 toward the skin surface and seats the needle (not shown) into a skin surface (not shown). Further, the drive spring 120 is configured to maintain contact with, and prevent retraction or rearward movement of the needle hub 208 after insertion.

As shown in FIG. 6, the top 202 and bottom 204 of the set 200 are configured to rotatably lock together using feet 216 of the top 202, and shoulders 218 of the bottom 204. Openings 220 are provided in the top 202 to allow the tabs 214 to extend from within the device for turning the body 206 relative to the hub 208 for alignment and activation.

A rotatable tube set connector 222 can then be coupled with the top 202 to complete the set. The connector 222 can comprise a cylindrical member 224 to engage a similarly shaped opening in the needle hub 208 through an opening in the top 202. The cylindrical member 224 can comprise a recess 226 into which an O-ring or other seal (not shown) can be provided. A fluid path 225 is established between an infusion pump tube (not shown) and the needle (not shown) via the assembly of the rotatable tube set connector 222 with the set.

As noted above, each driving spring 18, 120 and 210 is configured to insert an exemplary needle at a controlled high rate of speed, of 3.3 ft/sec. (1.0 m/sec.) up to and including those greater than 10 ft/sec. (3.0 m/sec.). Depending upon cannula sharpness, such a terminal velocity produces more reliable results for intradermal insertions of short (i.e., 1.5 mm) needle or cannula. The spring diameter, pitch, and material, all contribute to the spring constant. This constant and the total travel of the spring once released can be manipulated to produce the desired velocity T.

In an exemplary embodiment, the free length of the driving spring can be 38 mm, and the rate can be 0.05 N/mm, but embodiments are not limited thereto. In the up position (i.e., compressed), the length of the driving spring is 6.5 mm, but embodiments are not limited thereto. Therefore, the force F Up is:

$$F\ Up = k \cdot x = 0.05\ \text{N/mm} \times (38-6.5)\text{mm} = 0.05\ \text{N/mm} \times 31.5\ \text{mm}$$

$$F\ Up = 1.58\ N$$

In the skin position, where the needle is just touching the skin, the length of the spring is 6.5+1.5 mm=8 mm. Therefore, the force F Skin is:

$$F\ Skin = k \cdot x = 0.05\ \text{N/mm} \times (38-8)\text{mm} = 0.05\ \text{N/mm} \times 30\ \text{mm}$$

$$F\ Skin = 1.50\ N$$

In the down position, the length of the spring is 10.5 mm. Therefore, the force F Down is:

$$F\ Down = k \cdot x = 0.05\ \text{N/mm} \times (38-10.5)\text{mm} = 0.05\ \text{N/mm} \times 27.5\ \text{mm}$$

$$F\ Down = 1.38\ N$$

Each of these experimental Lengths was calculated using currently available engineering simulation software, such as a CAD program.

In the up position, the needle is recessed from the skin surface 1.5 mm, but embodiments are not limited thereto. Therefore, the needle is accelerated by the spring for a distance of 1.5 mm until the tip of the needle comes into contact with the skin. In an exemplary embodiment, the weight of the driven components is 4.1 g. The weight of the needle, needle holder, and needle assembly can be considered negligible. Therefore, the speed of the driven components, V, can be calculated at the point the where the needle contacts the skin surface to be:

Work Done=Change in Kinetic Energy $$F \times d = \tfrac{1}{2}\ m \times (V^2 - U^2)$$

where u=0 m/sec, $$\tfrac{1}{2}(1.58\ N + 1.50\ N) \times 1.5\ \text{mm} - 3\ \text{mm} = \tfrac{1}{2} \times 4.1\ \text{g} - 3\ \text{g} \times V^2$$

$$V = 1.06\ \text{m/sec}$$

In the exemplary calculation, the effects of friction in the system are ignored, and a constant acceleration is assumed. The actual acceleration decreases, since, as the driven components descend, the spring relaxes and the force is reduced. However, for purposes of the exemplary embodiments described herein, constant acceleration is assumed.

In each exemplary embodiment described above, the integrated ballistic inserter requires fewer operational steps and requires fewer parts than previously available inserter and set combinations. Notably, a separate inserter is not needed with these devices, thereby reducing the burden on users to carry the device and the amount of waste generated. Further, a removable inserter is not provided with these devices, thereby reducing the risk of movement to the infusion set when removing the inserter. The issue of a separate, reusable or disposable inserter is removed by integrating the cannula deployment mechanism into the hub of the device that remains attached to the patient.

Although the embodiments described above are preferably used for intradermal injections, each can be equally well used for subcutaneous injections.

Further, one or more of the exemplary embodiments of the present invention can be provided with a skin contacting adhesive layer and backing. Precise insertion is achieved by first securing the infusion set to the infusion site via the adhesive, which permits the user to activate the integrated ballistic inserter at the proper alignment and insert the needle. In doing so, the needle is driven into the skin surface at a controlled high rate of speed to minimize the risk of tenting at needle insertion. Further, the adhesive at or very near the insertion site secures the skin surface and further minimizes tenting of the skin surface during insertion.

In an exemplary use of the embodiments of the present invention, proper insertion of the infusion set into the delivery site consists of straightforward steps. For example, a backing (not shown) is peeled off the skin adhesive layer of the infusion set, and the infusion set is adhered to the skin surface in the area of the desired infusion site. The user then releases the driving spring by pulling a tab or rotating an arm, thereby inserting the needle into the skin surface of the infusion site. The use can then attach the tube set connection to the set and then prime the infusion set and deliver insulin or other medicament to the infusion site via the attached infusion pump (not shown).

Further, the integrated ballistic inserter and set ensure proper alignment and positioning. Most inserters on the market are either oversized, to ensure an insertion force perpendicular to the skin surface, or are thin and portable, which can lead to misaligned insertion. In the exemplary embodiments of the present invention, by first adhering or "locking" the outer skin adhesive of the infusion set to the skin surface, the integrated ballistic inserter is aligned properly for needle insertion. Accordingly, the exemplary embodiments of the present invention can include a relatively small inserter which is properly aligned with the infusion site at a time of use.

Such a system and method further allows the use of a small intradermal needle, or microneedle, which can be placed perpendicular to the skin surface, and which is isolated from outside forces, thereby maintaining position and causing less pain to the user during use. Still further, by infusing into the intradermal layer of the skin, the exemplary embodiments of the present invention offer the potential for better absorption of the insulin when compared to subcutaneous delivery systems. In doing so, it may be possible for the typical user to both consume less insulin and maintain a better medicament regime. It will be appreciated that multiple needles or microneedles can be used, if desired, in place of a single needle or microneedle.

As noted above, other intradermal infusion set concepts are at risk of tenting, which is the undesired effect where skin is deflected at or during insertion, creating a shape associated with a tent. In doing so, the skin surface tents during needle insertion rather than needle penetration into the skin. However, since the present invention provides a needle which is inserted at a controlled high rate of speed, of 3.3 ft/sec. (1.0 m/sec.) up to and including those greater than 10 ft/sec. (3.0 m/sec.), and wherein the skin surface is secured at the insertion site, the exemplary embodiments of the present invention reduce this risk and ensure more precise needle insertion depth.

In current steel cannula infusion sets which deliver to the subcutaneous layer, the needle is not isolated from any undesired outside forces which may cause pain when translated to the needle and the needle moves within the skin. Also, other intradermal devices face problems of premature or otherwise undesired needle removal when the device is bumped if the needle is not isolated from the outside forces.

In the exemplary embodiments of the present invention, the intradermal needle is isolated from outside forces by several features. The tops are provided to shield the sensitive needle hubs from direct contact with external forces. Separate adhesive layers can be used to secure separate elements of the set to the skin surface. Further, the tube connection can be rotatable without affecting set adhesion to the skin surface. The needle hub is held in the down (lowered or extended) position by the continued presence of the activation spring. Proper inserter alignment is accomplished by providing a solid, fixed foundation for the user to release the ballistic inserter drive spring. Such a solid, fixed foundation is provided by the skin adhesive. The skin adhesive secures the set at a desired orientation, such that the ballistic inserter is also at a desired orientation of use. Accordingly, precise, repeatable insertions are accomplished via the adhesion.

Still further, many commercial sets require the use of a separate or removable inserter. In the exemplary embodiments of the present invention described herein, the user does not have to carry a separate inserter or load the infusion set onto the inserter. The user is also not required to remove the inserter, or parts of the inserter, from the positioned infusion set. The integrated system allows the user more freedom from carrying and loading a separate inserter resulting in improved convenience and simpler operation.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. An integrated inserter, comprising:
a top portion;
a bottom portion that locks to said top portion by rotational alignment; and
a release mechanism including:
  a body surrounding a needle hub and needle, said body being enclosed in said top portion and said bottom portion; and
  a spring disposed in said body and configured to urge said needle hub and needle into a down position upon release, wherein said spring is configured to insert said needle into the skin at a controlled rate of speed; wherein
said release mechanism is configured to releasably secure at least one of said spring and said needle hub in an up position and to release at least one of said spring and said needle hub from said up position when said body is turned relative to said needle hub.

2. An integrated inserter as claimed in claim 1, wherein said body has at least one arm extending from said body, said body comprises at least one alignment opening configured to interfere with said needle hub and releasably secure at least one of said spring and said needle hub in an up position.

3. An integrated inserter as claimed in claim 1, further comprising
a tube set connector.

4. An integrated inserter as claimed in claim 1, wherein said spring comprises a length of about 38 mm and a rate of about 0.05 N/mm.

5. An integrated inserter as claimed in claim 1, wherein in said up position, a length of said spring is about 6.5 mm, and a force F Up is represented by a following equation:

$$F\ Up = k \cdot x = 0.05\ N/mm \times (38-6.5)mm\ 0.05\ N/mm \times 31.5\ mm$$

$$F\ Up = 1.58\ N.$$

6. An integrated inserter as claimed in claim 1, wherein in a skin contacting position, a length of said spring is about 8 mm, and a force F Skin is represented by a following equation:

$$F\ Skin = k \cdot x = 0.05\ N/mm \times (38-8)mm = 0.05\ N/mm \times 30\ mm$$

$$F\ Skin = 1.50\ N.$$

7. An integrated inserter as claimed in claim 1, wherein in said down position, a length of said spring is about 10.5 mm, and a force F Down is represented by a following equation:

$$F\ Down = k \cdot x = 0.05\ N/mm \times (38-10.5)mm = 0.05\ N/mm \times 27.5\ mm$$

$$F\ Down = 1.38\ N.$$

8. An integrated inserter as claimed in claim 1, wherein in said up position, said needle is recessed from a skin surface about 1.5 mm, such that said needle is accelerated by said spring for a distance of 1.5 mm before said needle comes into contact with said skin surface, and a speed Of said needle and needle hub, V, at said point where said needle contacts said skin surface is represented by a following equation:

Work Done=Change in Kinetic Energy $F \times d = \frac{1}{2} m \times (V2 - U2)$ where u=0 m/sec, $\frac{1}{2}(1.58\ N + 1.50\ N) \times 1.5\ mm\mathrm{-}3\ mm = \frac{1}{2} \times 4.1\ g\mathrm{-}3\ g \times V2$ V=1.06 m/sec.

9. An integrated inserter as claimed in claim 1, further comprising at least one adhesive layer disposed upon a surface of said bottom portion.

10. An integrated inserter, comprising:
a top portion;
a bottom portion; and
a release mechanism including:
  a body fully enclosed in top portion and the bottom portion, the body surrounding a needle hub and needle; and
  a spring disposed in said body and configured to urge said needle hub and needle from an up position into a skin contacting position, and further into a down position when said body is turned relative to said needle hub, said spring being configured to insert said needle at a controlled rate of speed; wherein
said release mechanism is configured to releasably secure at least one of said spring and said needle hub in said up position, said body having at least one arm extending from within said top portion to the outside of said top portion.

11. An integrated inserter as claimed in claim 10, wherein said body comprises at least one alignment opening configured to interfere with said needle hub and releasably secure at least one of said spring and said needle hub in an up position.

12. An integrated inserter as claimed in claim 10, further comprising a tube set connector.

13. An integrated inserter as claimed in claim 10, wherein, and one of a single-bevel, tri-bevel or 5-bevel, and having a length between 1.0 mm and 10 mm, and
wherein said spring comprises a length of about 38 mm in a relaxed state, and has a rate of about 0.05 N/mm.

14. An integrated inserter as claimed in claim 10, wherein in said up position, a length of said spring is about 6.5 mm, and a force F Up is represented by a following equation:

$F\ Up = k \cdot x = 0.05\ N/mm \times (38 - 6.5) mm = 0.05\ N/mm \times 31.5\ mm$ F Up=1.58 N.

15. An integrated inserter as claimed in claim 10, wherein in a skin contacting position, a length of said spring is about 8 mm, and a force F Skin is represented by a following equation:

$F\ Skin = k \cdot x = 0.05\ N/mm \times (38 - 8) mm = 0.05\ N/mm \times 30\ mm$ F Skin=1.50 N.

16. An integrated inserter as claimed in claim 10, wherein in said down position, a length of said spring is about 10.5 mm, and a force F Down is represented by a following equation:

$F\ Down = k \cdot x = 0.05\ N/mm \times (38 - 10.5) mm = 0.05\ N/mm \times 27.5\ mm$ F Down=1.38 N.

17. An integrated inserter as claimed in claim 10, wherein in said up position, said needle is recessed from a skin surface about 1.5 mm, such that said needle is accelerated by said spring for a distance of 1.5 mm before said needle comes into contact with said skin surface, and a speed of said needle and needle hub, V, at said point where said needle contacts said skin surface is represented by a following equation:

Work Done=Change in Kinetic Energy $F \times d = \frac{1}{2}\ m \times (V2 - U2)$ where u=0 m/sec, $\frac{1}{2}(1.58\ N + 1.50\ N) \times 1.5\ mm\mathrm{-}3\ mm = \frac{1}{2} \times 4.1\ g\mathrm{-}3\ g \times V2$ V=1.06 m/sec.

18. An integrated inserter as claimed in claim 10, wherein said at least one arm extends substantially perpendicularly from a centerline of said body.

19. A method for targeting a desired needle placement depth into an upper skin surface, comprising the steps of:
placing an integrated inserter upon an infusion site;
rotating a release mechanism of said integrated inserter relative to a body of said integrated inserter;
releasing a stored energy device upon said rotation;
urging and directly contacting a needle hub of said integrated inserter by said stored energy device to move a needle of said integrated inserter into said infusion site, said needle being fixed to said needle hub, wherein said needle is moved into said infusion site at a controlled rate of speed; and
using said stored energy device to hold said needle of said integrated inserter in said infusion site.

20. A method as claimed in claim 19, wherein said stored energy device comprises a spring and in an up position, a length of said spring is about 6.5 mm and a force F Up is represented by a following equation:

$F\ Up = k \cdot x = 0.05\ N/mm \times (38 - 6.5) mm = 0.05\ N/mm \times 31.5\ mm$ F Up=1.58 N.

21. A method as claimed in claim 20, wherein in a skin contacting position, a length of said spring is about 8 mm, and a force F Skin is represented by a following equation:

$F\ Skin = k \cdot x = 0.05\ N/mm \times (38 - 8) mm = 0.05\ N/mm \times 30\ mm$ F Skin=1.50 N.

22. A method as claimed in claim 20, wherein in a down position, a length of said spring is about 10.5 mm, and a force F Down is represented by a following equation:

$F\ Down = k \cdot x = 0.05\ N/mm \times (38 - 10.5) mm = 0.05\ N/mm \times 27.5\ mm$ F Down=1.38 N.

23. A method as claimed in claim 20, wherein in said up position, said needle is recessed from a skin surface about 1.5 mm, such that said needle is accelerated by said spring for a distance of 1.5 mm before said needle comes into contact with said skin surface, and a speed of said needle and needle hub, V, at said point where said needle contacts said skin surface is represented by a following equation:

Work Done=Change in Kinetic Energy $$F \times d = \frac{1}{2} m \times (V2 - U2)$$

where u=0 m/sec, $$\frac{1}{2}(1.58\ N + 1.50\ N) \times 1.5\text{mm} - 3\text{ mm} = \frac{1}{2} \times 4.1\ g - 3\ g \times V2$$

V=1.06 m/sec.

\* \* \* \* \*